US00PP08372P

United States Patent [19]

Snow

[11] Patent Number: Plant 8,372

[45] Date of Patent: Sep. 14, 1993

[54] BEGONIA PLANT NAMED SCENTIMENT BLUSH

[75] Inventor: Andrew B. Snow, Watsonville, Calif.

[73] Assignee: Golden State Bulb Growers, Watsonville, Calif.

[21] Appl. No.: 881,810

[22] Filed: May 12, 1992

[51] Int. Cl.[5] ..... A01H 5/00

[52] U.S. Cl. ..... Plt./87.18

[58] Field of Search ..... Plt./87.18

*Primary Examiner*—James R. Feyrer

*Attorney, Agent, or Firm*—Foley & Lardner

[57] ABSTRACT

A distinct cultivar of Begonia plant named Scentiment Blush, characterized by its distinct fragrance, fully double male flowers which do not produce pollen or male productive parts, pale blush pink main flower color with yellowing at center and deeper pink on reverse side, plant habit which is full and pendulous with numerous shoots each of which produces 4 to 5 penduncles with 1 to 2 male flowers.

1 Drawing Sheet

The present invention relates to a new and distinctive cultivar of begonia plant, botanically known as begonia *Tuberhybrida pendula* and known by the cultivar name Scentiment Blush.

The new cultivar was discovered by the inventor Andrew B. Snow as a seedling from a controlled crossing of B. Love Song as the seed parent with B. Sweety II as the pollen parent.

Asexual reproduction by leaf cuttings has produced the unique features of the new cultivar through successive propagations at my enterprise in Watsonville, Calif.

The following characteristics distinguish the new begonia from both its parents and other begonias commercially known and used in the floriculture industry:

1. The flower has a definite and distinct fragrance that can be described as quite sweet and lingering but not overpowering. It is often compared to the scent of a fragrant rose bloom. The fragrance is most pronounced when the temperature is between 70° and 80° F.

2. The male flowers are fully double and do not produce pollen or male reproductive parts under normal growing conditions.

3. The main flower color is a pale blush pink, with the back of the main petals a deeper pink. The petal color changes to yellow at the center of the flower with some flowers showing some yellow streaking.

4. The plant habit is full and pendulous with numerous flower shoots (4–6 or more). Each flowering shoot will produce anywhere from 4–6 penduncles with 1 or 2 male flowers on each during the growing season.

There are no known begonia cultivars with which the new cultivar can be meaningfully compared. The color variance and gradation is unique, as is the distinct fragrance.

The accompanying colored photographs taken Sept. 20, 1991 illustrate the overall appearance and flower color and shape of the new cultivar when grown in a 10" plastic pot. The top photograph is a side elevational view of the new cultivar. The bottom photograph shows the top surface of two flowers and the underside of one flower. The colors are as true as it is reasonably possible to obtain in colored reproductions of this type.

The following is a detailed description of my new begonia cultivar based on plants produced under commercial practices in Watsonville, Calif. Color references are made to The Royal Horticultural Society Colour Chart except where general terms of ordinary dictionary significance are used.

Parentage: Begonia cultivar "Love Song" (seed parent) × Begonia cultivar "Sweety III" (pollen parent).

Propagation:

A. *Type cutting.*—Leaf.

B. *Time to root.*—24 to 30 days at 21° C. summer; 32 to 38 days at 21° C. winter.

C. *Rooting habit.*—Abundant, fibrous, dendritic.

D. *Time for shoot development.*—Slow, 10 to 14 weeks in summer and up to 16 weeks in winter.

Plant description:

A. *Form.*—Low mounding, pendulous; herbaceous.

B. *Habit of growth.*—Slow, uniform growth with numerous shoots and moderate branching habit at full growth. The plant is well rounded with a height of about 10 to 15 inches, and up to 20" pendulous shoots. The width is approximately 24 inches.

C. *Foliage.*—Simple, alternate, and borne on semi-rigid petioles 3 to 6 inches in length. 1. Size: At maturity the leaves reach 6 to 8 inches from base to apex, and at their widest point the leaves are up to 6 inches in width. 2. Shape: Triangular-cordate with acuminate tip between rounded based lobes. 3. Texture: Firm, crisp, but not brittle; sparsely hirtellous on both surfaces. 4. Margin: Doubly serrate. 5. Color: Young foliage, top side:slightly darker than 143A; under side:147C. Mature foliage, top side:146A and B; under side:147C. 6. Venation: Reticulate.

Flowering description:

A. *Flowering habits.*—Flowering is presented on a pendulous raceme. Often, but not always, secondary male and female flowers will develop below the primary male and female flowers. Some peduncles have a solitary male flower, while others may have a solitary male flower accompanied by either a solitary secondary male flower or matching female flower and occasionally a secondary male and female flower.

B. *Natural flowering season.*—Natural flowering season is the summer and fall months.

C. *Flower buds.*—Flat, nearly round, tending towards bell shaped.

D. *Flowers borne.*—On small pedicels originating from long (5 to 8 inches) axillary peduncles, resulting in a solitary male flower, a solitary male and one or two female flowers, and occasionally secondary male and female flowers as raceme develops.

E. *Quantity.*—Flowering ranges from 2 to 5 flowers per peduncle and numerous (3 to 5) peduncles per shoot, with 5 to 7 shoots per plant.

F. *Tepals.*—1. Shape: Oval to tear drop shaped. 2. Color: Top side in winter when opening, white, fading to 36D; underside 49C fading to 36D to white. 3. Number of tepals: 35 to 50 on male flowers, 5 on female flowers. 4. Size of tepals:

Outer (male), up to 2 $\frac{3}{4}''\times2\frac{1}{2}''$, inner $\frac{3}{8}''\times\frac{3}{8}''$. 5. Flower size: Male, $5''\times5''$; female, $3\frac{1}{2}''\times3\frac{1}{2}''$.

G. *Reproductive organs.*—1. Stamens: None. 2. Pistils: a. Stigma shape: Multi-lobed, color 15A. b. Style color: 15A. c. Ovaries: Number 3, size $\frac{3}{8}''$ to $\frac{5}{8}''$, color 144C.

Disease resistance: Scentiment Blush has shown excellent disease resistance to date.

I Claim:

1. A new and distinct cultivar of begonia plant named Scentiment Blush, as illustrated and described.

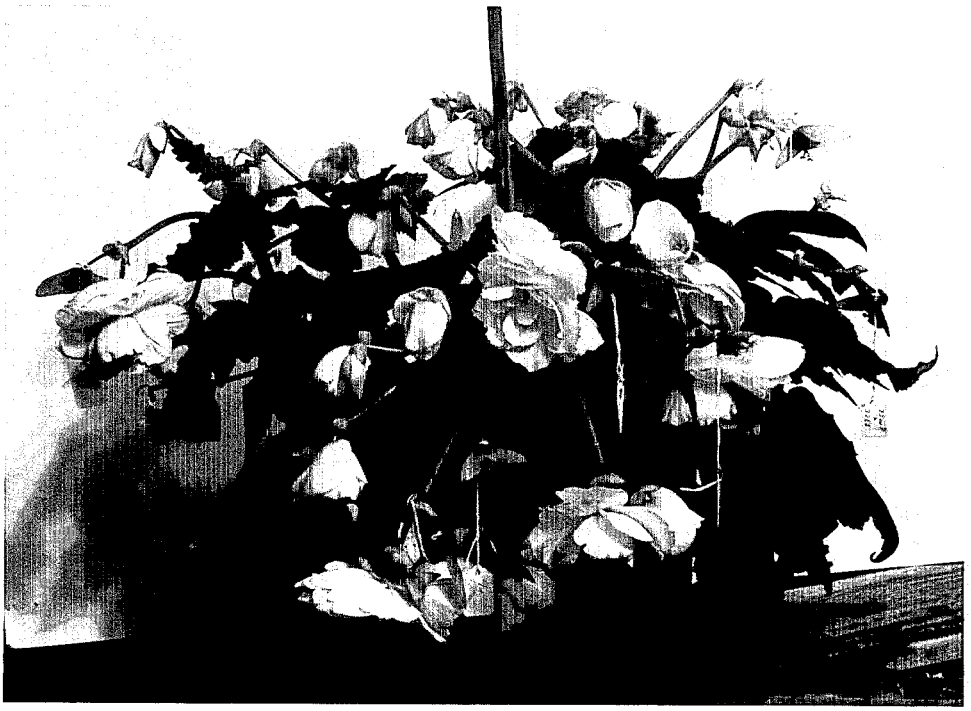
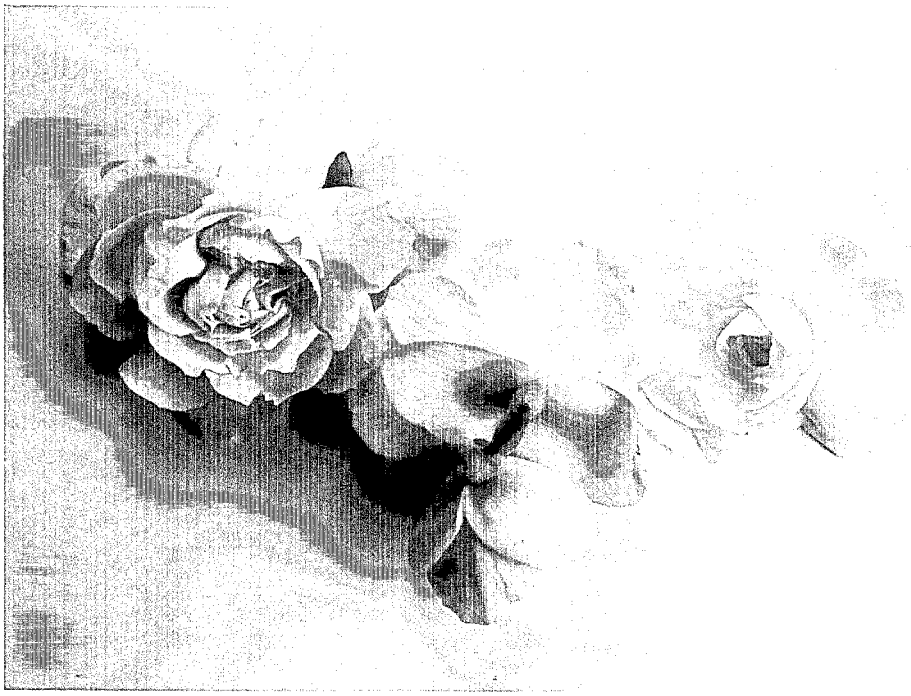

* * * * *